US008527227B2

(12) United States Patent
Shioda

(10) Patent No.: US 8,527,227 B2
(45) Date of Patent: Sep. 3, 2013

(54) METHOD AND DEVICE FOR MEASURING ELECTROMAGNETIC WAVE

(75) Inventor: Michinori Shioda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 282 days.

(21) Appl. No.: 12/985,163

(22) Filed: Jan. 5, 2011

(65) Prior Publication Data

US 2011/0168896 A1    Jul. 14, 2011

(30) Foreign Application Priority Data

Jan. 8, 2010    (JP) ................................ 2010-002482

(51) Int. Cl.
*G01R 23/16*    (2006.01)
(52) U.S. Cl.
USPC ................. 702/77; 702/70; 702/76; 702/124; 702/190; 327/106
(58) Field of Classification Search
USPC .......................................................... 702/77
See application file for complete search history.

(56) References Cited

U.S. PATENT DOCUMENTS

| | | | |
|---|---|---|---|
| 5,939,721 A | 8/1999 | Jacobsen | |
| 6,078,047 A * | 6/2000 | Mittleman et al. | 250/338.1 |
| 7,599,570 B2 * | 10/2009 | Berkner | 382/265 |
| 2004/0193065 A1 * | 9/2004 | Houben | 600/509 |
| 2008/0149819 A1 | 6/2008 | Zhdaneev | |
| 2008/0183466 A1 * | 7/2008 | Nongpiur et al. | 704/226 |
| 2009/0103395 A1 | 4/2009 | Willen | |
| 2011/0184654 A1 * | 7/2011 | Ben-David et al. | 702/19 |

FOREIGN PATENT DOCUMENTS

JP    10-153547 A    6/1998

OTHER PUBLICATIONS

Neelamani et al., ForWaRD: Fourier-Wavelet Regularized Deconvolution for Ill-conditioned Systems, IEEE Transactions on Signal Processing, vol. 52, No. 2, Feb. 2004.*
Donoho D. et al., "Adapting to Unkown Smoothness via Wavelet Shrinkage", Journal of the American Statistical Association, XP007908507, vol. 90, No. 432, Dec. 1, 1995, pp. 1200-1224.
Donoho D. L. et al., "Threshold Selection for Wavelet Shrinkage of Noisy Data", Department of Statistics, Stanford University, Stanford, CA 94305, IEEE, XP010145191, Nov. 3, 1994, pp. 24a and 25a.
Deng L. et al., "Wavelet Denoising of Chirp-Like Signals in the Fourier Domain", Computational Neuro-Engineering Laboratory, University of Florida, ECE Department, EB-453, Gainesville, FL 32611, XP010341015, May 30, 1999, pp. III-540 through III-543.
Ferguson B. et al., "De-Noising Techniques for Terahertz Responses of Biological Samples", Microelectronics Journal 32 (2001), XP004311553, Dec. 1, 2001, pp. 943-953.
Taswell C., "The What, How, and Why of Wavelet Shrinkage Denoising", Computing in Science and Engineering, XP003006305, vol. 2, No. 3, May 1, 2000, pp. 12-19.
Bradley Ferguson and Derek Abbott article entitled "De-noising techniques for terahertz responses of biological samples" published in Microelectronics Journal 32 (2001), pp. 943-953.
S. Mickan et al., "Analysis of System Trade-Offs for Terahertz Imaging", Microelectronics Journal 31, 2000, pp. 503-514.
Taswell C., "The What, How, and Why of Wavelet Shrinkage Denoising", Computing in Science and Engineering, vol. 2, Issue 3, Jun. 30, 2000, pp. 12-19.

* cited by examiner

*Primary Examiner* — Andrew Schechter
*Assistant Examiner* — John Kuan
(74) *Attorney, Agent, or Firm* — Canon USA Inc. IP Division

(57) ABSTRACT

A waveform acquiring unit acquires a time waveform of an electromagnetic wave. The time waveform is decomposed into wavelet expansion coefficients by wavelet transform. Influence levels of the respective wavelet expansion coefficients to a spectrum are calculated. The wavelet expansion coefficients are weighted based on at least the influence levels of the wavelet expansion coefficients to the spectrum. The weighted wavelet expansion coefficients are converted into time waveforms by inverse wavelet transform. Thus, the time waveforms that holds spectrum information needed for spectroscopic analysis and has a reduced noise is provided.

14 Claims, 10 Drawing Sheets

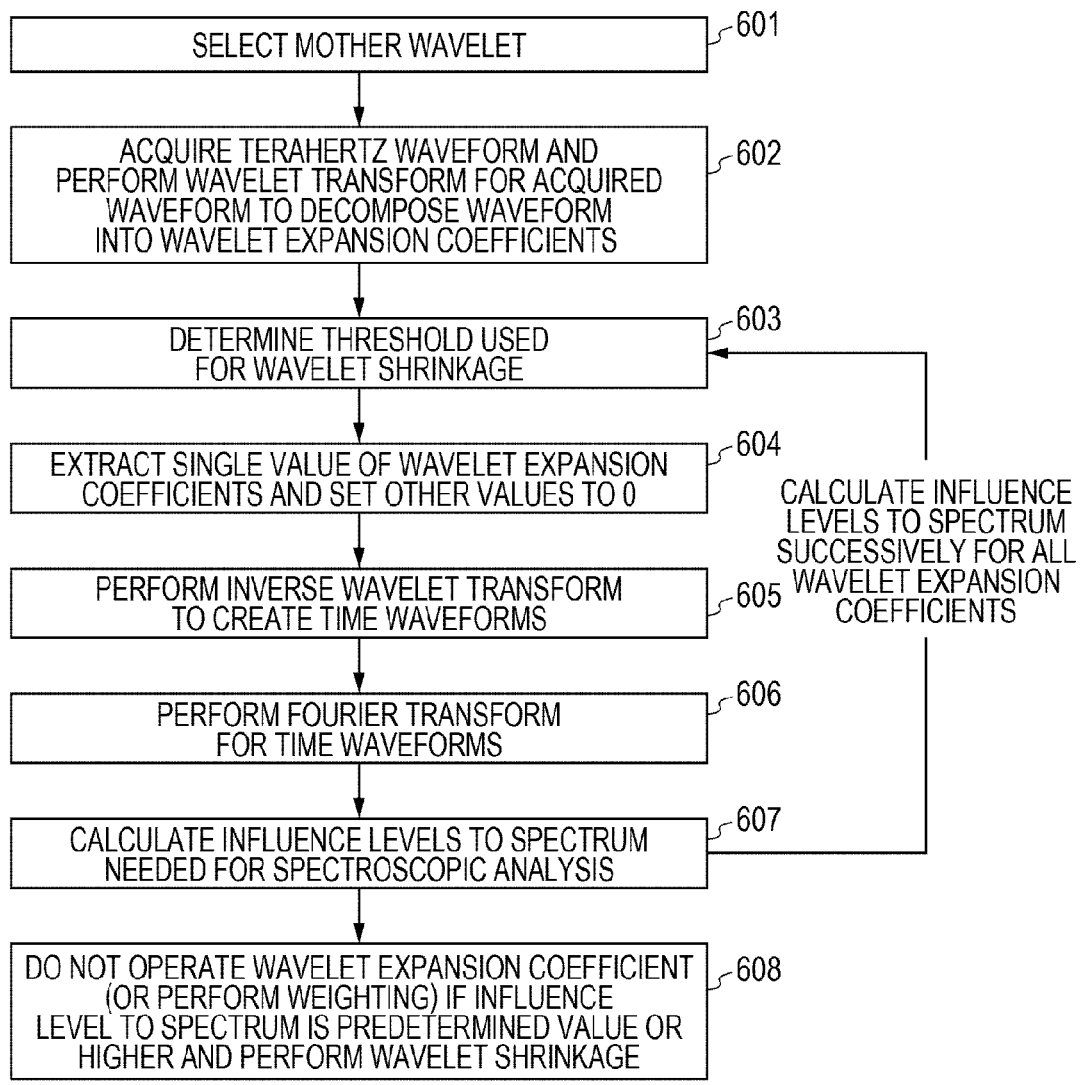

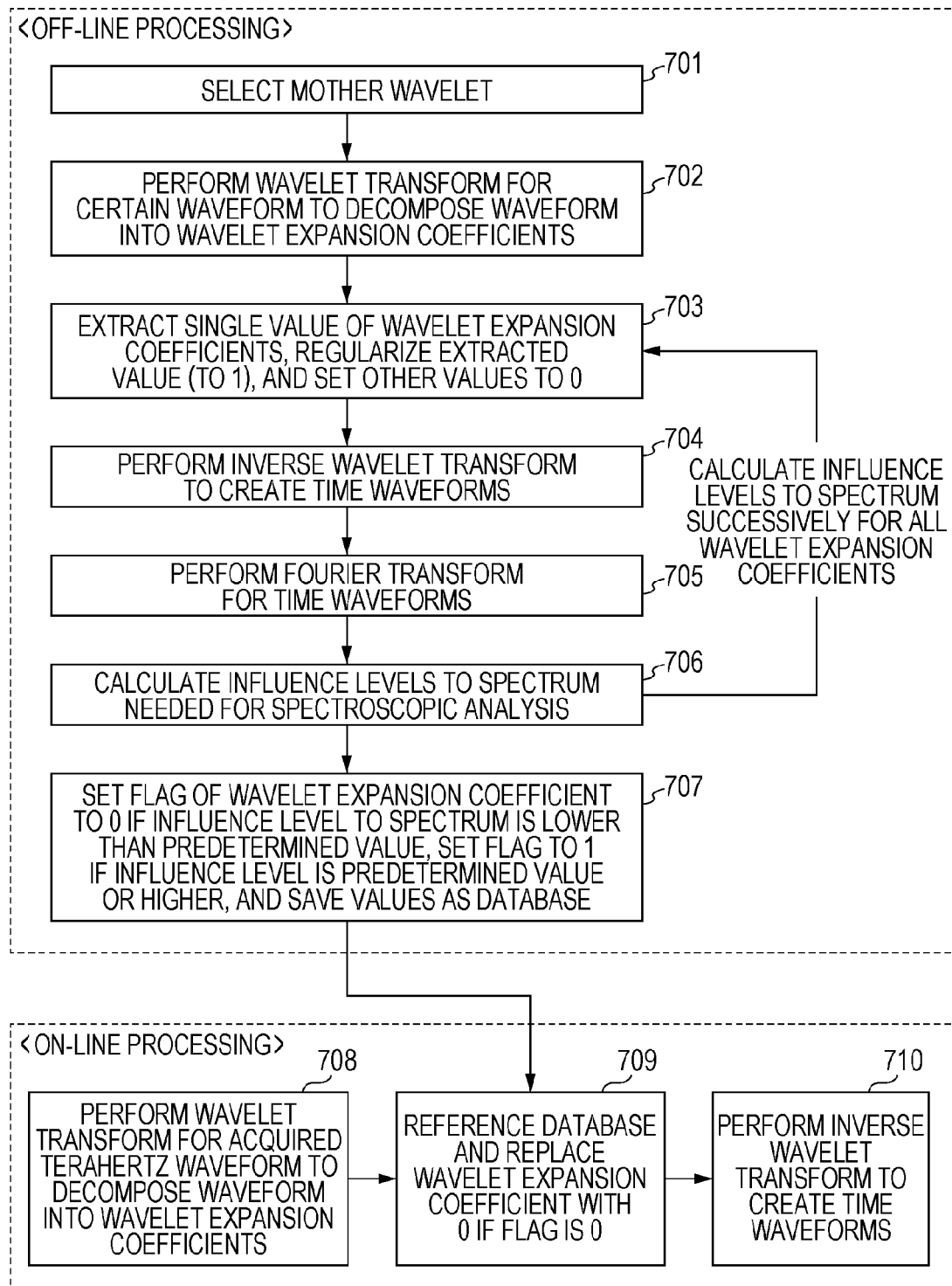

METHOD AND DEVICE FOR MEASURING ELECTROMAGNETIC WAVE

CROSS REFERENCE TO RELATED APPLICATIONS

This application claims priority from Japanese Patent Application No. 2010-002482 filed Jan. 8, 2010, the disclosure of which is hereby incorporated by reference herein in its entirety.

BACKGROUND OF THE INVENTION

1. Field of the Invention

The present invention relates to a technique of measurement for information of, for example, a waveform of an electromagnetic wave, and more particularly to a measurement device and a measurement method with the use of a signal processing technique by wavelet analysis for a terahertz wave.

2. Description of the Related Art

In recent years, non-destructive spectroscopic imaging with the use of a terahertz wave, and terahertz time-domain spectroscopy (THz-TDS) for investigating the properties of a substance with the use of a terahertz wave pulse are being actively studied. Japanese Patent Laid-Open No. 10-153547 discloses a method relating to image processing for imaging with a terahertz wave. The method uses wavelet analysis for information compression or peak detection. Also, "De-noising techniques for terahertz responses of biological samples," Microelectronics Journal 32 (2001), pp. 943-953 discloses a method including converting a time waveform of a terahertz wave by wavelet transform, and setting a set of values of wavelet expansion coefficients that is smaller than a threshold to 0 (threshold processing). By performing inverse wavelet transform after manipulating wavelet expansion coefficients in this way, a time waveform in which the noise component is reduced can be acquired. In "De-noising techniques for terahertz responses of biological samples," Microelectronics Journal 32 (2001), pp. 943-953, signal to noise (SN) ratios are compared with each other for various mother wavelets after noise components are reduced, and the mother wavelet that reduces the noise component most effectively is determined. The noise component is mainly a white noise that appears in all frequency ranges. The component of the white noise has not much correlation with the mother wavelet. Hence, the white noise appears near 0 for each expansion coefficient.

With the conventional technique, to increase the SN ratio of the measured time waveform of the terahertz wave, noise reduction is performed by wavelet transform (wavelet shrinkage). Unfortunately, this method may delete spectrum information that is needed for identifying a substance in the course of signal processing. The conventional method is enough if only necessary is acquiring image data with a good SN ratio. However, if spectroscopic data on a substance in an image should be acquired simultaneously when the image is acquired with the terahertz wave as the electromagnetic wave, it may be difficult to use a terahertz waveform after the signal processing is performed, to identify the substance (spectroscopic analysis).

SUMMARY OF THE INVENTION

According to an aspect of the present invention, an electromagnetic wave measurement method for measuring an electromagnetic wave includes acquiring a time waveform of the electromagnetic wave; decomposing the time waveform of the electromagnetic wave into wavelet expansion coefficients by wavelet transform; calculating influence levels of the respective wavelet expansion coefficients to a spectrum in a predetermined measurement range; weighting the wavelet expansion coefficients based on at least the influence levels of the respective wavelet expansion coefficients to the spectrum; and converting the weighted wavelet expansion coefficients into time waveforms by inverse wavelet transform.

According to another aspect of the present invention, an electromagnetic wave measurement device that measures an electromagnetic wave includes a wave acquiring unit configured to acquire a time waveform of the electromagnetic wave; a decomposing unit configured to decompose the time waveform of the electromagnetic wave into wavelet expansion coefficients by wavelet transform; a calculating unit configured to calculate influence levels of the respective wavelet expansion coefficients to a spectrum in a predetermined measurement range; a weighting unit configured to weight the wavelet expansion coefficients based on at least the influence levels of the respective wavelet expansion coefficients to the spectrum; and a converting unit configured to convert the weighted wavelet expansion coefficients into time waveforms by inverse wavelet transform.

With the device and method according to the aspects of the present invention, the wavelet expansion coefficients, which are weighted based on the influence levels of the wavelet expansion coefficients to the spectrum, are converted into the time waveforms by the inverse wavelet transform. Accordingly, the spectrum information needed for the spectroscopic analysis can be held while the noise is reduced by the wavelet transform. Thus, for example, when terahertz imaging such as tomography is performed, the SN ratio of imaging data can be increased by the wavelet transform, and the substance included in the imaging object can be identified.

Further features of the present invention will become apparent from the following description of exemplary embodiments with reference to the attached drawings.

BRIEF DESCRIPTION OF THE DRAWINGS

FIG. 6 is a flowchart according to a first embodiment of the present invention.

FIG. 7 is a flowchart according to a second embodiment of the present invention.

DESCRIPTION OF THE EMBODIMENTS

Figure 1A:
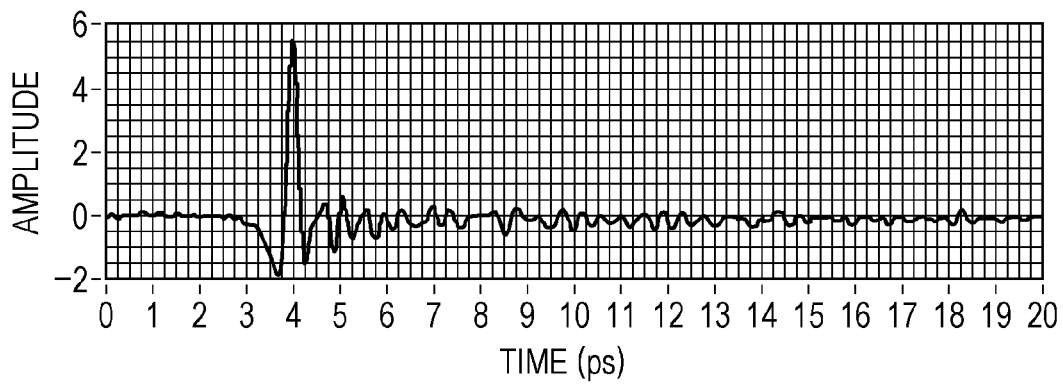
FIGS. 1A to 1D illustrate a time waveform etc. of a terahertz wave acquired by THz-TDS.

Embodiments of the present invention will be described below. With a method and a device according to the embodiments of the present invention, when signal processing by wavelet transform is performed for a time waveform of an electromagnetic wave, the following measures are taken to hold spectrum information that is needed for spectroscopic analysis and to reduce unnecessary information including a noise. In particular, a time waveform of an electromagnetic wave is acquired, and the time waveform is decomposed into wavelet expansion coefficients by wavelet transform. Then, influence levels of the respective wavelet expansion coefficients to a spectrum in a predetermined measurement range are calculated, and the wavelet expansion coefficients are weighted based on the influence levels of the wavelet expansion coefficients to the spectrum. Then, the weighted wavelet expansion coefficients are converted into time waveforms by inverse wavelet transform. The weighting may be performed by taking into account a threshold that is used for the wavelet transform, in addition to the influence levels to the spectrum.

Based on this idea, an electromagnetic wave measurement method according to a basic embodiment of the present invention includes the steps of acquiring a waveform, decomposing, calculating, weighting, and converting, as described above. In the acquisition of the waveform, for example, if a terahertz wave (an electromagnetic wave including a frequency component in a range from 30 GHz to 30 THz) is used as an electromagnetic wave, a time waveform of the terahertz wave is acquired by THz-TDS. However, it is not limited thereto. If an electric signal in a range from direct current (DC) to about several gigahertzes is used as an electromagnetic wave, a time waveform may be acquired by an oscilloscope. In the decomposition, a decomposition level for the wavelet expansion coefficients may be desirably selected. In general, as the number of expansion coefficients is larger, the decomposition becomes finer. The signal processing by the wavelet transform may be wavelet shrinkage that operates values of wavelet expansion coefficients (values correlated with a mother wavelet) by using a threshold.

In the calculation, the influence levels of the respective wavelet expansion coefficients to the needed spectrum information are calculated. The influence level to spectrum information is a level of closeness between a spectrum and a wavelet expansion coefficient (i.e., the level of correlation with characteristic spectrum information, such as an absorption spectrum or the like). For example, the influence levels of the respective expansion coefficients to the spectrum are calculated such that only a single value is extracted from the decomposed expansion coefficients and at least a single frequency power (signal intensity) of a Fourier spectrum of that expansion coefficient is added to the extracted value. For example, if the frequency needed for the spectroscopic analysis is in a range from 0.5 to 0.8 THz, a value added with powers within the range is used as the influence level. If a plurality of frequency ranges are needed, powers within these ranges may be added. For example, if frequencies needed for the spectroscopic analysis are from 0.1 to 0.5 THz, and from 1 to 1.5 THz, powers within these ranges may be added.

Alternatively, a single wavelet expansion coefficient, which has been decomposed in advance, may be extracted and at least a single frequency power of a Fourier spectrum of that expansion coefficient may be added to the extracted value, so that the added value is used as the influence level. The frequencies to be selected do not have to be continuous. For example, only a frequency of 0.5 THz may be used, or two frequencies of 0.6 THz and 1 THz may be used. In this case, regularization can be performed by extracting a single wavelet expansion coefficient and setting the value of the extracted expansion coefficient to 1 (regularization to 1). When the at least single frequency power is added, a frequency power may be weighted and then added, so that the value is used as the influence level of the wavelet expansion coefficient to the spectrum. For example, a weight of 1 may be assigned to a certain frequency, and a weight of 0.5 may be assigned to the other frequencies. The weight may be multiplied by the power of the frequency, and the resulted value may be added, so that the added value is used as the influence level of the wavelet expansion coefficient to the spectrum. At this time, the powers of the frequencies in the Fourier spectrum of the electromagnetic wave acquired in the calculation may be directly used for the weighting (the same result as that described above can be obtained). In this embodiment, the power is used to determine the influence level. However, the influence level may be determined with not only a complex amplitude, which is the power, but also a phase. In the Fourier transform, waveforms with different phases at different timings have equivalent frequencies (spectra), but have different waveforms. Thus, to distinguish these two waveforms from one another and to assign weights, phase information may be additionally used.

For example, the weighting may be performed as follows. A certain threshold is set, and a wavelet expansion coefficient that is smaller than the threshold is selected. Then, it is checked whether the influence level of the selected wavelet expansion coefficient to the spectrum is higher than a certain influence level. If the influence level is higher, the value of the wavelet expansion coefficient is not operated to be 0. In contrast, if the influence level of the selected wavelet expansion coefficient to the spectrum is lower than the certain influence level, the value of the wavelet expansion coefficient is set to 0.

Based on this idea, an electromagnetic wave measurement device according to a basic embodiment of the present invention may include a waveform acquiring unit, a decomposing unit, a calculating unit, a weighting unit, and a converting unit. Further, the device may include a saving unit and an adjusting unit. The influence level is determined by the calculating unit in the same manner as the method described in the measurement method. The weighting is performed by the weighting unit in the same manner as the method described in the measurement method. The saving unit saves as a database the weights that are assigned depending on a measurement object and an environmental condition, such as the humidity, air pressure, and element characteristic. For example, if the humidity is different, even though the same sample is measured, a time waveform of a terahertz wave to be measured becomes different. Since moisture absorbs a terahertz wave, absorption of water vapor may slightly vary depending on whether the humidity is high or low. Hence, the weights to be assigned are changed accordingly, and saved as the database. If an electromagnetic wave generating element is changed (for example, if the shape of an antenna of a photoconductor is changed), the frequency characteristic of an electromagnetic wave is changed. This phenomenon corresponds to that the frequencies are weighted. Thus, the weights are saved as the database. As described above, the weighting is performed in advance depending on the measurement object and the environmental condition. The resultant weights are saved as the database in a computer. For example, a large weight may be assigned to a spectral range that is characteristic of a measurement object of interest, and a small weight may be assigned to a spectral range that is characteristic of an environmental condition of non-interest. The adjusting unit adjusts the weights of the wavelet expansion coefficients in accordance with the aforementioned features. The weight of the wavelet expansion coefficient used for the signal processing is changed depending on the measurement object. The converting unit can convert the wavelet expansion coefficient after its weight is adjusted, into a time waveform by inverse wavelet transform.

Next, specific embodiments for an electromagnetic wave measurement device and an electromagnetic wave measurement method according to the present invention will be described below.

First Embodiment

Figure 1B:
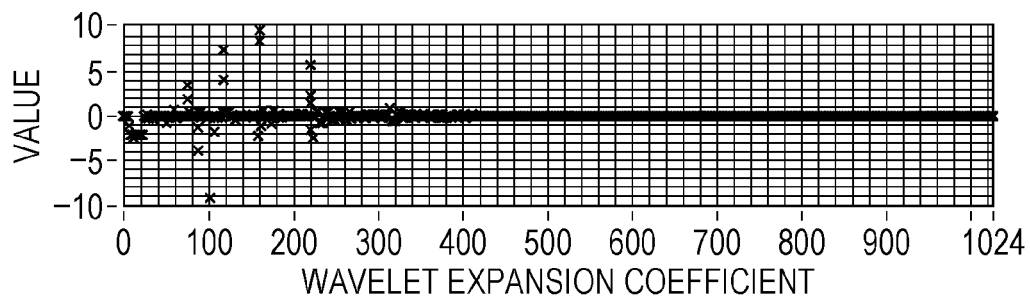

A first embodiment will now be described. FIG. 1A illustrates a time waveform of a terahertz wave acquired by THz-TDS. Maltose having a spectrum that is characteristic of a terahertz range is used as a measurement object. The time waveform involves a system noise caused by a measurement system during measurement. In this embodiment, the number of measured data points is 1000. Zero padding is performed for the shortage of data if needed so that the number of data points becomes the power-of-two. FIG. 1B illustrates a distribution obtained by decomposing the acquired time waveform into wavelet expansion coefficients by wavelet transform. When the wavelet transform is performed, for example, Coiflets 4 (coif4) is used as a mother wavelet, and the level is 10. The wavelet expansion coefficients in FIG. 1B are successively extracted, and inverse wavelet transform is performed. Accordingly, the wavelet expansion coefficients are reconstructed into time waveforms. Then, the acquired time waveforms are converted by Fourier transform. Hence, a spectrum corresponding to the time waveforms are obtained. If time waveforms acquired by the inverse wavelet transform for all wavelet expansion coefficients in FIG. 1B are added, the time waveform in FIG. 1A can be obtained.

Figure 1C:
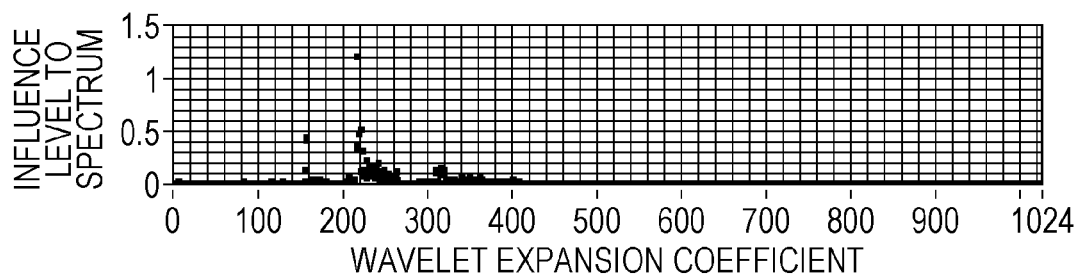
Figure 1D:
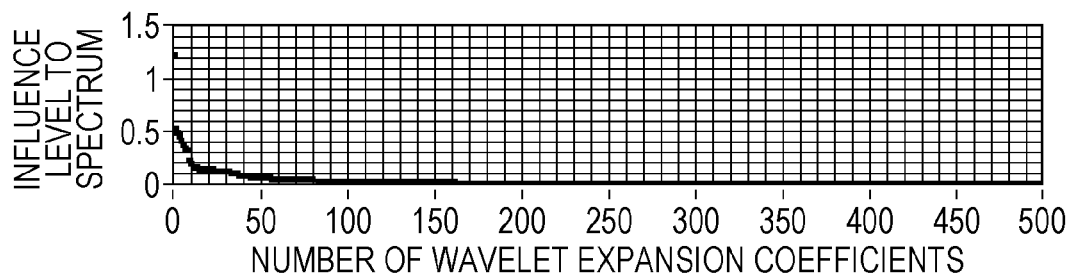
Figure 2A:
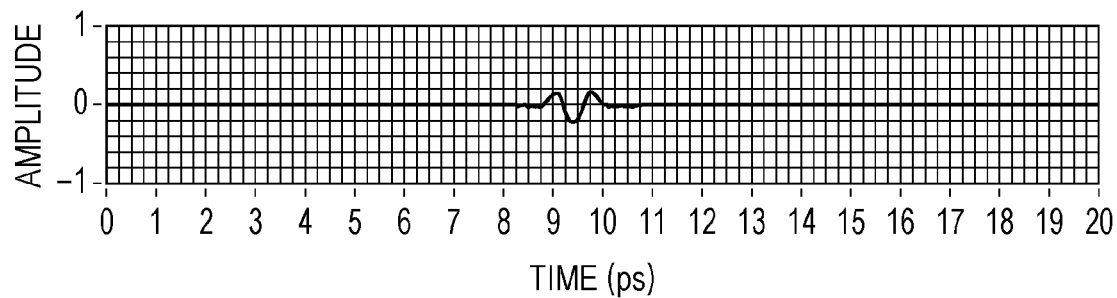
FIGS. 2A and 2B illustrate a time waveform and a spectrum relating to a wavelet expansion coefficient 167 (coif4).
Figure 2B:
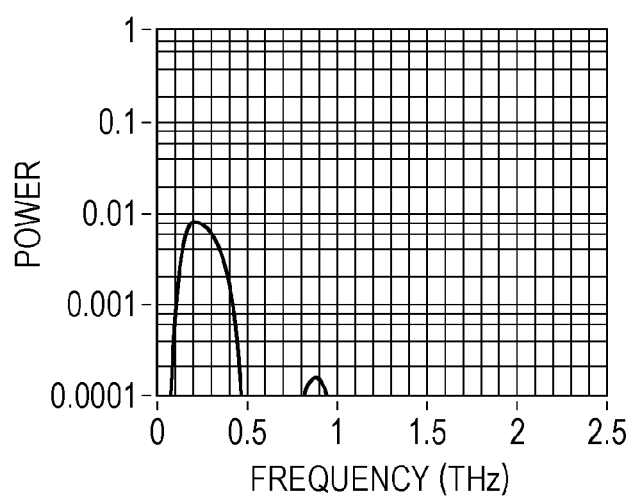

FIG. 2A illustrates a time waveform relating to a wavelet expansion coefficient 167 when the wavelet expansion coefficient 167 is reconstructed by the inverse wavelet transform. FIG. 2B is a spectrum relating to the wavelet expansion coefficient 167 when the time waveform is converted by the Fourier transform. The vertical axis in FIG. 2B has a logarithmic scale. FIG. 1C illustrates the wavelet expansion coefficients and the influence levels to the spectrum when a frequency range for integration is from 0.3 to 1 THz. FIG. 1D illustrates the influence levels to the spectrum when the influence levels in FIG. 1C are arranged in order from a higher one. The number of wavelet expansion coefficients having high influence levels to the spectrum can be found from FIG. 1D. In this embodiment, the frequency range for integration is a single range. However, a plurality of ranges may be provided. Also, the calculation does not have to be the simple integration, and may include weighting the time waveforms based on frequencies and adding the time waveforms. For example, a weight for a frequency range having a characteristic spectrum may be changed from a weight for the other frequency range.

The wavelet shrinkage sets a threshold, and if a value of a wavelet expansion coefficient is smaller than the set threshold, sets the value to 0. In contrast, in this embodiment, even though the value of the wavelet expansion coefficient is smaller than the threshold, if the influence level of the wavelet expansion coefficient to the spectrum is a certain value or higher as shown in FIG. 1C, the value is not set to 0. In particular, a threshold A and a threshold B are set. The threshold A relates to the value of the wavelet expansion coefficient and is known as the wavelet shrinkage. The threshold B relates to the influence level to the spectrum and is unique to the embodiment. If the value of the wavelet expansion coefficient is smaller than the threshold A and if the influence level to the spectrum is smaller than the threshold B, the value of the wavelet expansion coefficient is set to 0. The other values of the wavelet expansion coefficients are held unchanged. This operation corresponds to that the values of the wavelet expansion coefficients are multiplied by 0 or 1. The use of the expansion coefficient is represented by 0 or 1.

Figure 3A:
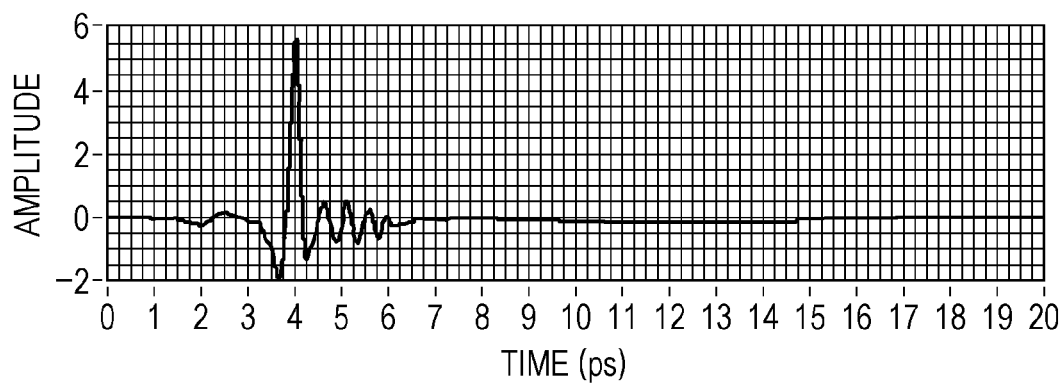
FIGS. 3A and 3B illustrate a time waveform after wavelet transform is performed by using only a threshold A, and the result when Fourier transform is performed for the time waveform.
Figure 3B:
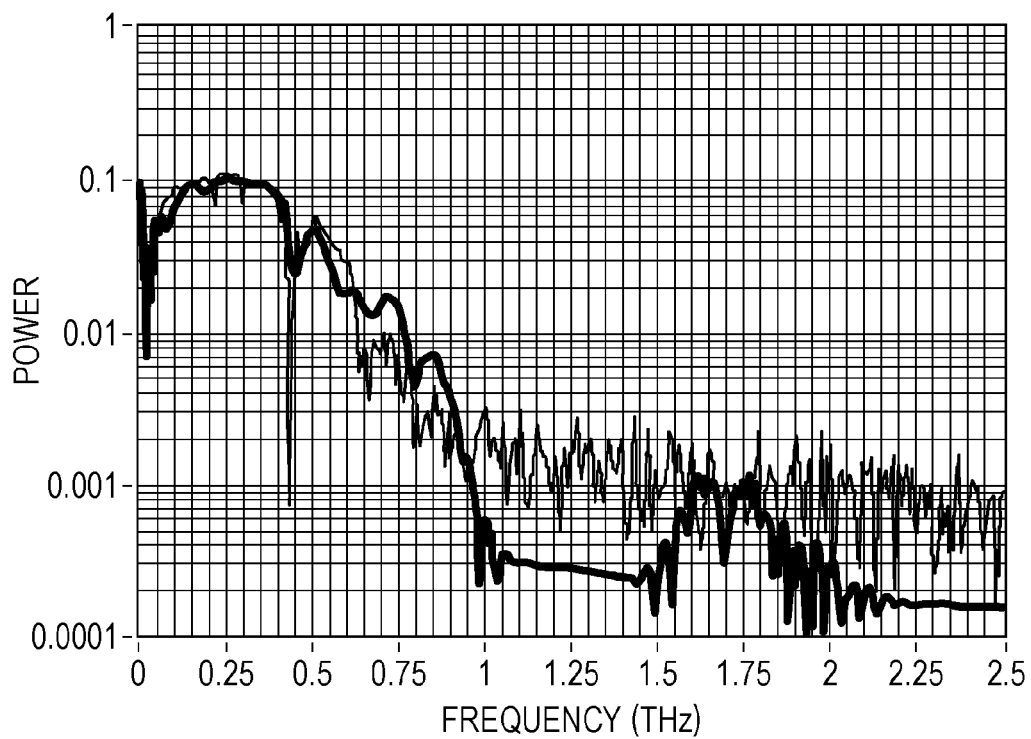

FIG. 3A illustrates a time waveform after the inverse wavelet transform as the result of that the threshold A is set to 1.4 and the wavelet shrinkage by the conventional method is performed for comparison. The thick line in FIG. 3B is the result of that FIG. 3A is converted by the Fourier transform. The thin line in FIG. 3B is the result of that the time waveform before the wavelet transform (the waveform in FIG. 1A) is converted by the Fourier transform. Comparing the thick line with the thin line in FIG. 3B, it can be found that the absorption spectrum of the thin line located near 0.4 THz is almost removed by the wavelet transform.

Figure 4A:
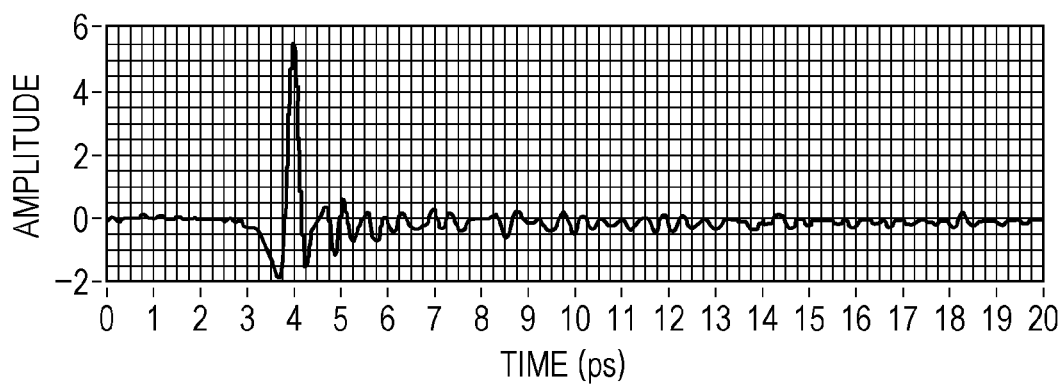
FIGS. 4A and 4B illustrate a time waveform after wavelet transform is performed by using thresholds A and B, and the result when Fourier transform is performed for the time waveform.
Figure 4B:
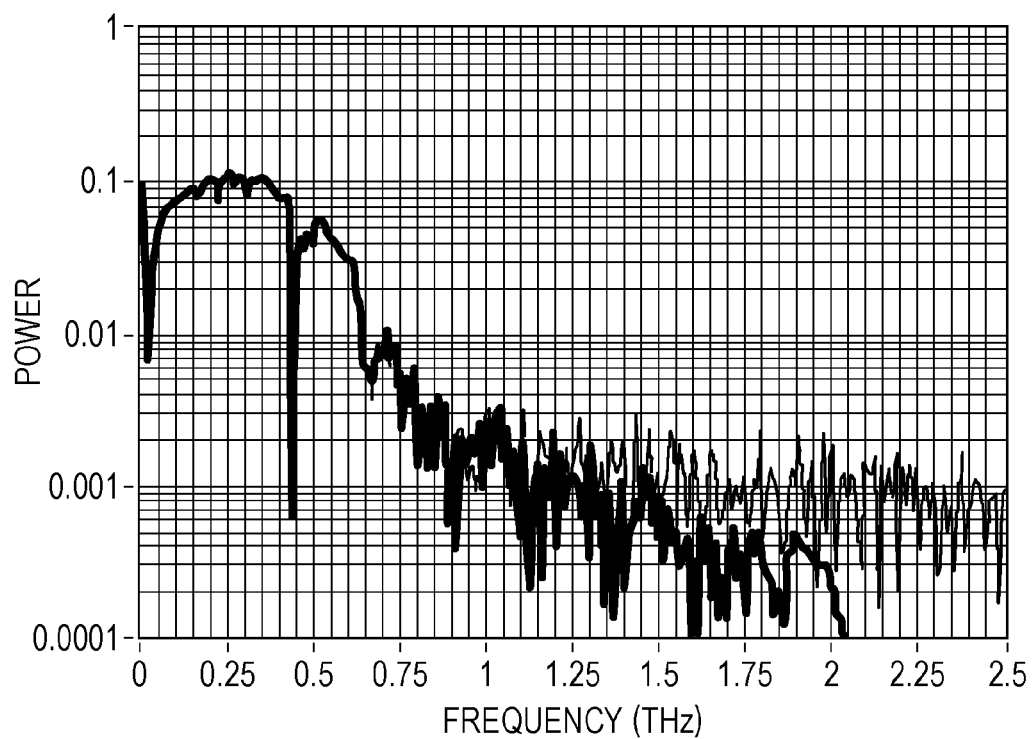

FIG. 4A illustrates a time waveform by the method according to this embodiment. In particular, the frequencies in the range from 0.3 to 1 THz are integrated respectively for the wavelet expansion coefficients, to calculate the influence levels to the spectrum. FIG. 4A illustrates the time waveform after the inverse wavelet transform is performed while the threshold operation is not performed for the wavelet expansion coefficients whose influence levels to the spectrum are the threshold B or higher. The threshold A is 1.4, and the threshold B is 0.005. The thick line in FIG. 4B is obtained by converting the time waveform in FIG. 4A, in which the noise is reduced in this embodiment, by the Fourier transform. The thin line in FIG. 4B is the same as the thin line in FIG. 3B. Comparing the thick line with the thin line in FIG. 4B, it can be found that the absorption spectrum located near 0.4 THz, the spectrum which is characteristic of maltose, is saved, and a noise in a range of 1 THz or higher, the noise which is unnecessary information, is reduced.

Figure 5A:
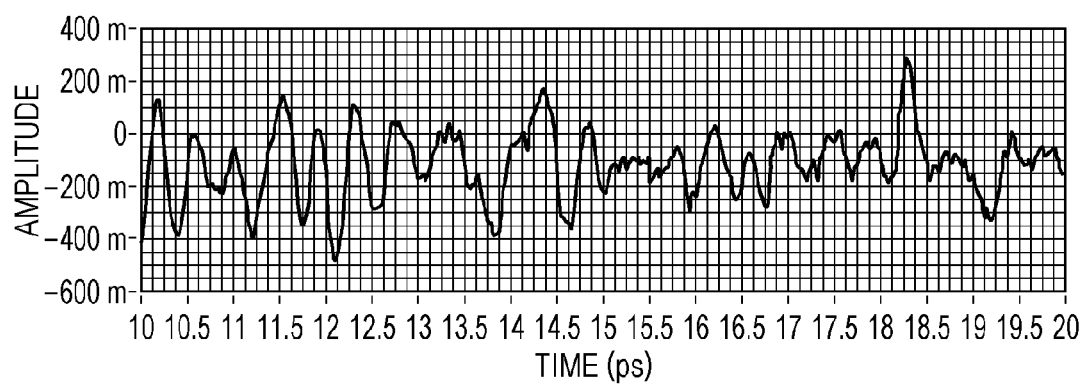
FIGS. 5A and 5B are enlarged views of parts of FIG. 1A and FIG. 4A.
Figure 5B:
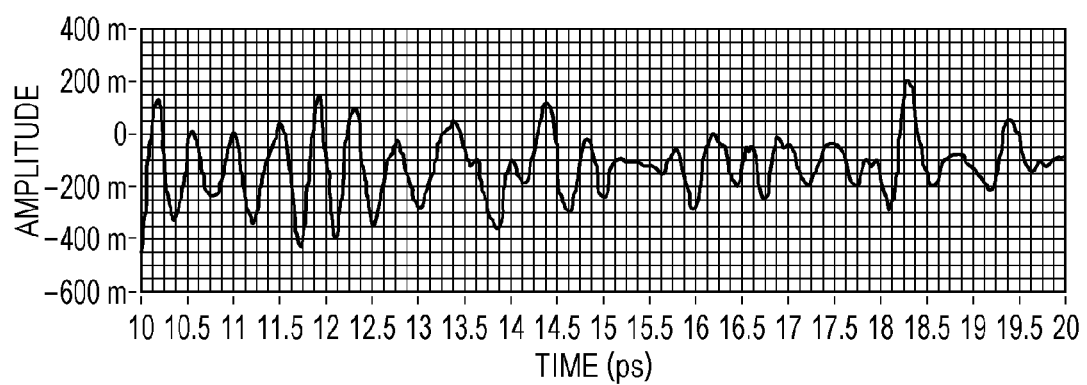

FIGS. 5A and 5B are enlarged views of parts of FIGS. 1A and 4A. Referring to FIG. 5A, it is found that a noise (a high-frequency noise) is included. In contrast, referring to FIG. 5B, it is found that since the noise is reduced, the waveform is smooth.

FIG. 6 is a flowchart for the aforementioned process. In step 601, a proper mother wavelet is selected. In step 602, the waveform acquiring unit acquires a time waveform of an electromagnetic wave. The acquired time waveform is converted by wavelet transform, so that the waveform is decomposed into wavelet expansion coefficients. In step 603, a threshold that is used for the wavelet transform (wavelet shrinkage) is determined. In step 604, a single value is extracted from the wavelet expansion coefficients, and the other values of the wavelet expansion coefficients are set to 0. In step 605, the extracted wavelet expansion coefficient is converted by inverse wavelet transform, and a time waveform is created. In step 606, the time waveform is converted by Fourier transform. In step 607, an influence level to a spectrum, the level which is needed for the spectroscopic analysis, is calculated.

The steps 604 to 607 are performed for all wavelet expansion coefficients. Based on the result, in step 608, the wavelet shrinkage is performed while the wavelet expansion coefficients whose influence levels to the spectrum are a certain value or higher are not operated. In step 608, the wavelet expansion coefficients are weighted based on at least the influence levels of the wavelet expansion coefficients to the spectrum, and the wavelet shrinkage is performed. Then, the weighted wavelet expansion coefficients are converted into time waveforms by the inverse wavelet transform. Thus, the time waveforms of the electromagnetic wave that hold the spectrum information needed for the spectroscopic analysis with the reduced noise can be obtained.

Second Embodiment

Next, a second embodiment will be described. FIG. 7 is a flowchart according to the second embodiment. In the first embodiment, the influence levels of the wavelet expansion coefficients to the spectrum are calculated during the measurement. The second embodiment differs from the first embodiment in that influence levels of wavelet expansion coefficients to a spectrum are calculated in advance. In the second embodiment, information relating to the wavelet expansion coefficients used for the wavelet transform is saved as a database in advance, and wavelet transform is performed by using the information.

The description will be given with reference to FIG. 7. In step 701, a mother wavelet is determined. In this embodiment, Daubechies 10 (db10) is selected, and the level is 10. In step 702, the wavelet transform is performed for a time waveform of a certain terahertz wave, and the waveform is decomposed into expansion coefficients. Here, it is important to decompose the waveform into the wavelet expansion coefficients by a program. Thus, the time waveform of the terahertz wave may be any kind of waveform. In step 703, a single value is extracted from the decomposed expansion coefficients, the value is regularized, and the other values of the expansion coefficients are set to 0. In this embodiment, the extracted value is regularized to 1. This operation is performed in order to extract a series of expansion coefficients. Thus, the values of the expansion coefficients are unnecessary. After the values of the expansion coefficients are replaced, in step 704, inverse wavelet transform is performed to create a time waveform. In step 705, Fourier transform is performed for the time waveforms. Then, similarly to the method described in the first embodiment, in step 706, an influence level to the spectrum, the level which is needed for the spectroscopic analysis, is calculated. Influence levels are calculated for all wavelet expansion coefficients, so that the influence levels to the spectrum, the levels which are needed for the spectroscopic analysis, are calculated. The steps 703 to 706 are performed for all wavelet expansion coefficients.

Then, in step 707, flags of the wavelet expansion coefficients whose influence levels to the spectrum are lower than a certain value (corresponding to the threshold B that is described in the first embodiment and is characteristic of the present invention) are set to 0, and flags of the expansion coefficients whose influence levels are the certain value or higher are set to 1. The flag 0 indicates that the influence level is none. The flag 1 indicates that the influence level is held unchanged. The information is saved as the database provided in the computer. The steps 703 to 707 are performed by off-line processing before a measurement object is measured.

Next, on-line processing will be described. In step 708, a time waveform of a terahertz wave from the measurement object is measured (acquired) by the waveform acquiring unit through the THz-TDS. The wavelet transform is performed by using the selected mother wavelet, and the waveform is decomposed into wavelet expansion coefficients. Then, in step 709, information relating to the wavelet expansion coefficients to be used by the wavelet transform are extracted, the information which corresponds to the measurement object and the environmental condition, such as the humidity, air pressure, and element characteristic of the waveform acquiring unit, from the database. Specifically, flag information is extracted. The flag information indicates which expansion coefficient is replaced with 0 and which expansion coefficient is used unchanged. Using the expansion coefficient unchanged is equivalent to that the weighting is performed based on frequency powers of a Fourier spectrum of the terahertz wave acquired in the on-line processing. In particular, the thin line in FIG. 3B (FIG. 4B) is obtained by performing the Fourier transform for the time waveform of the terahertz wave before the wavelet transform is performed. As indicated by the thin line, the element characteristic is such that the power of the spectrum in the range from 0.1 to 1 THz decreases toward 1 THz. Owing to this, the influence level to the spectrum, the level which is needed for the spectroscopic analysis, may be calculated by correction (that is, weighting based on frequencies) such that the powers of the frequencies in the range become equivalent to each other. In this embodiment, however, the simple integration is employed without the correction. Thus, the weighting is performed merely based on the frequency powers in the Fourier spectrum of the element characteristic.

Then, in step 710, the expansion coefficients after the processing with the flag information are converted into time waveforms by the inverse wavelet transform. In this way, the spectrum information needed for the spectroscopic analysis can be held while the noise is reduced by the wavelet transform. In this embodiment, the threshold A, which is known as the wavelet shrinkage, is not used when the wavelet transform is performed. Alternatively, the threshold A may be used, and the information from the database may be reflected to only the expansion coefficients that are threshold A or smaller.

Figure 8A:
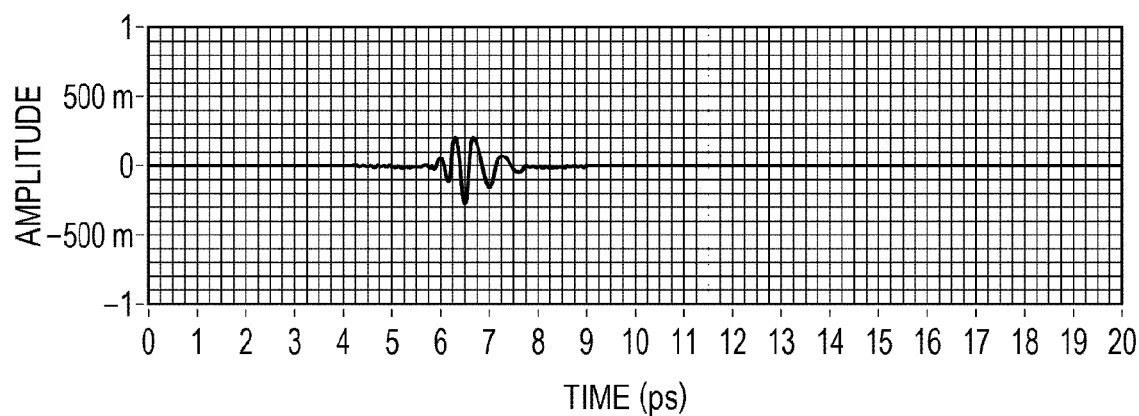
FIGS. 8A and 8B illustrate a time waveform and a spectrum relating to a wavelet expansion coefficient 200 (db10).
Figure 8B:
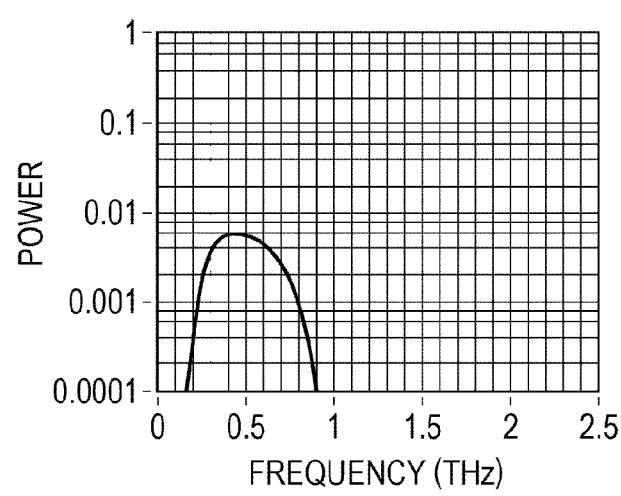
Figure 9A:
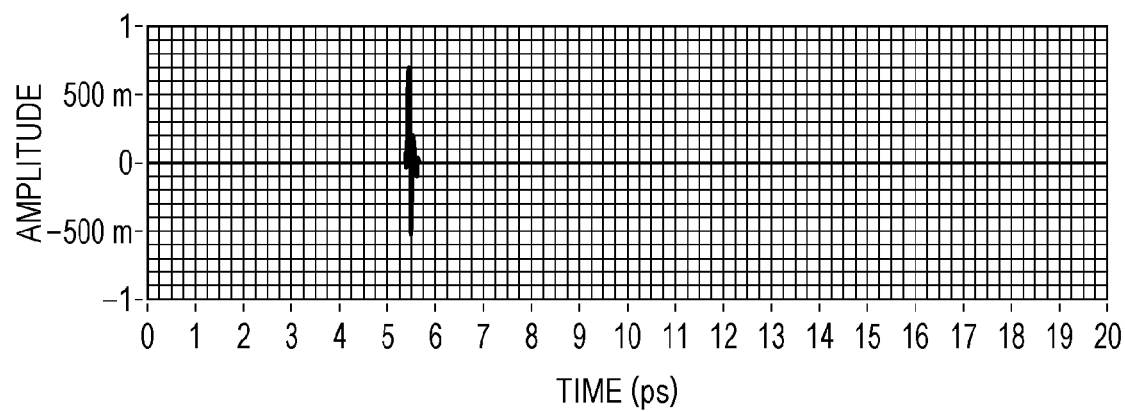
FIGS. 9A and 9B illustrate a time waveform and a spectrum relating to a wavelet expansion coefficient 800 (db10).
Figure 9B:
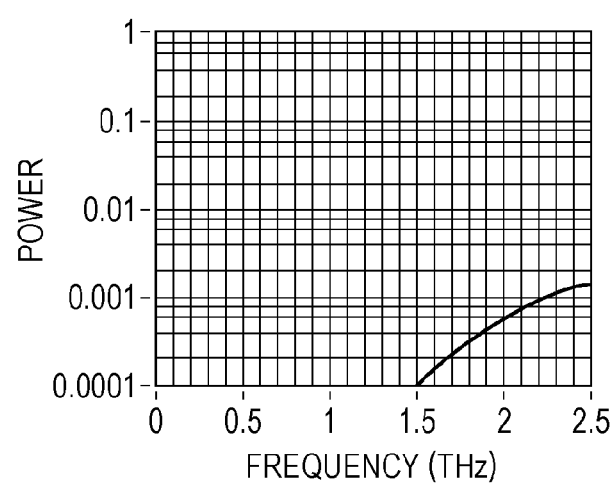

Flags for expansion coefficients will be described. FIG. 8A illustrates a time waveform when an expansion coefficient 200 is extracted, the value of the expansion coefficient 200 is set to 1, and the inverse wavelet transform is performed (refer to steps 703 and 704 described above). FIG. 8B is a spectrum of the time waveform in FIG. 8A (refer to step 705 described above). FIG. 9A is a time waveform in the case of an expansion coefficient 800. FIG. 9B is a spectrum of the time waveform in FIG. 9A. If a frequency range is from 0.3 to 1 THz to calculate the influence level to the spectrum, referring to FIG. 8B, it is found that a high influence level of the expansion coefficient 200 to the spectrum appears (refer to step 706 described above). In contrast, referring to FIG. 9B, it is found that no influence of the expansion coefficient 800 to the spectrum appears. Thus, by setting a proper threshold B, the flag for the expansion coefficient saved as the database may be 1 for the expansion coefficient 200, and may be 0 for the expansion coefficient 800 (refer to step 707 described above). This operation is applied to all expansion coefficients, and hence flags are set for all expansion coefficients. The set flag information is saved as the database in the computer (refer to step 707 described above). Other process is similar to that of the first embodiment.

Figure 10A:
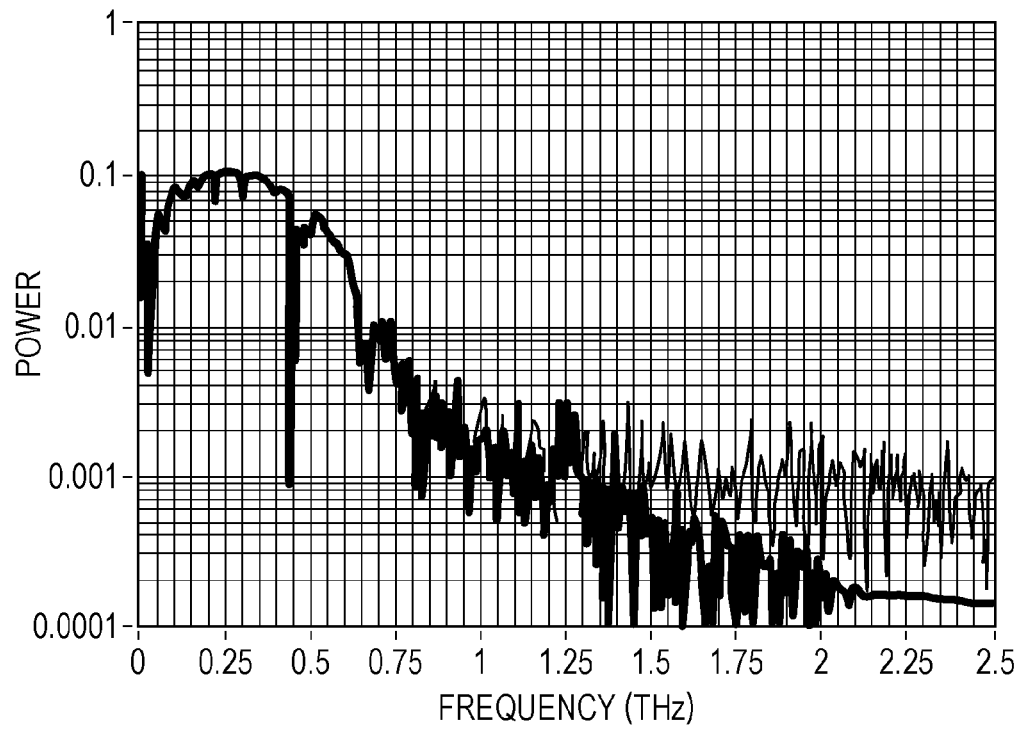
FIGS. 10A and 10B illustrate the result when Fourier transform is performed for the time waveform after a noise is reduced according to the second embodiment, and the configuration of a device according to an embodiment of the present invention.

FIG. 10A illustrates the result. The thick line in FIG. 10A is obtained by converting the time waveform, in which the noise is reduced by this embodiment, by the Fourier transform. The thin line in FIG. 10A is the same as the thin line in FIG. 3B. Comparing the thick line with the thin line in FIG. 10A, it is found that, in the thick line, the absorption spectrum located near 0.4 THz, the spectrum which is characteristic of maltose is saved, and a noise in a range of 1 THz or higher, the noise which is unnecessary information, is reduced. In the above description, the coif4 or db10 is used as a basis of the mother wavelet. However, other basis such as Symlets may be applied. When maltose is measured, the unnecessary information including noise can be efficiently reduced even if any of Coiflets 1 to 4 (coif1 to coif4), Symlets 2 to 5 (sym2 to sym5), and Daubechies 5 to 12 (db5 to db12) is used.

Third Embodiment

Figure 10B:
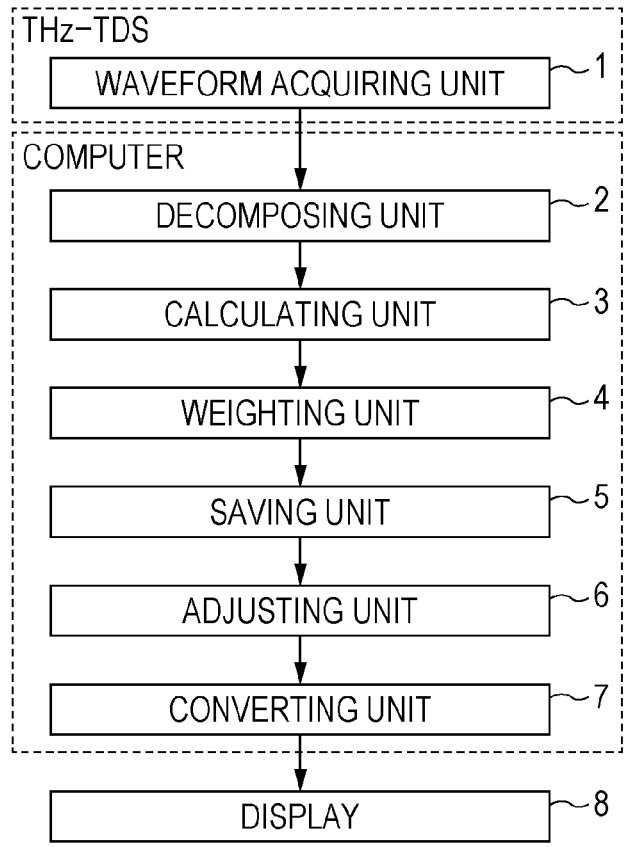

FIG. 10B illustrates an example of the configuration of a device according to a third embodiment of the present invention. A wavelet acquiring unit 1 acquires a time waveform of an electromagnetic wave. The acquisition is performed by THz-TDS, and hence a time waveform of a terahertz wave can be acquired. A decomposing unit 2 decomposes the time waveform of the terahertz wave into wavelet expansion coefficients by wavelet transform. A calculating unit 3 calculates influence levels of the respective wavelet expansion coefficients to a spectrum. The calculation method is similar to that described in the first embodiment. A weighting unit 4 weights the wavelet expansion coefficients based on a threshold used by the wavelet transform and the influence levels of the wavelet expansion coefficients to the spectrum (or based on only the influence levels to the spectrum). A saving unit 5 saves the weighted wavelet expansion coefficients as a database on the measurement object basis. An adjusting unit 6 adjusts the weights of the wavelet expansion coefficients depending on a measurement object. The weights have to be properly selected for the wavelet expansion coefficients depending on the measurement object. Thus, the weights for the wavelet expansion coefficients depending on the measurement object are selected from the database. Also, the selected weighted values of the wavelet expansion coefficients are adjusted depending on an environmental condition, such as a measurement condition or the like.

A converting unit 7 performs inverse wavelet transform for the wavelet expansion coefficients after the adjustment, to convert the wavelet expansion coefficients into time waveforms. In this embodiment, the decomposing unit 2, the calculating unit 3, the weighting unit 4, the saving unit 5, the adjusting unit 6, and the converting unit 7 are operated by a computer. The time waveforms acquired by the converting unit 7 are displayed on a display 8 that is connected with a personal computer.

Other Embodiment

Also, the present invention can be realized by performing the following processing. In particular, software (program) that realizes the functions according to any of the aforementioned embodiments may be supplied to a system or a device through a network or by any kind of storage media. A computer (or computer processing unit (CPU), micro-processing unit (MPU), and/or the like) included in the system or device reads and executes the program. Any kind of storage media may be used as long as the medium can store the program that is executed by the computer. The storage medium is a computer-readable storage medium that stores the program to cause the computer to execute the aforementioned electromagnetic wave measurement method.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An electromagnetic wave measurement method for measuring an electromagnetic wave, the method comprising:
   acquiring a time waveform of the electromagnetic wave;
   decomposing the time waveform of the electromagnetic wave into wavelet expansion coefficients by wavelet transform;
   calculating influence levels of the respective wavelet expansion coefficients to a spectrum in a predetermined measurement range;
   weighting the wavelet expansion coefficients, using a processor, based on at least the influence levels of the respective wavelet expansion coefficients to the spectrum; and
   converting the weighted wavelet expansion coefficients into time waveforms by inverse wavelet transform,
   wherein the calculation for the influence levels of the respective wavelet expansion coefficients to the spectrum includes:
      extracting a single value from the decomposed wavelet expansion coefficients,
      reconstructing the single value into a time waveform by the inverse wavelet transform,
      converting the reconstructed time waveform by Fourier transform,
      calculating a value as one of the influence levels by adding a signal intensity of at least a single frequency; the signal intensity being derived from the Fourier transform, and
      repeating the calculation for the respective wavelet expansion coefficients.

2. The electromagnetic wave measurement method according to claim 1, further comprising:
   saving as a database the weights of the wavelet expansion coefficients acquired by the weighting on a measurement object basis; and
   adjusting the weights of the wavelet expansion coefficients depending on the measurement object,
   wherein, in the conversion, the wavelet expansion coefficients whose weights are adjusted by the adjustment are converted into time waveforms by the inverse wavelet transform.

3. The electromagnetic wave measurement method according to claim 1, wherein, in the weighting, the wavelet expansion coefficients are weighted based on a threshold that is used by the wavelet transform, and the influence levels of the wavelet expansion coefficients to the spectrum.

4. The electromagnetic wave measurement method according to claim 1, wherein the value obtained by adding the signal intensity of the at least single frequency is a value that is obtained by weighting signal intensities of frequencies based on frequencies and adding the signal intensities.

5. The electromagnetic wave measurement method according to claim 1, wherein the electromagnetic wave is a terahertz wave including a frequency component in a range from 30 GHz to 30 THz.

6. A non-transitory storage medium storing a computer-readable program that causes a computer to execute the electromagnetic wave measurement method according to claim 1.

7. An electromagnetic wave measurement device that measures an electromagnetic wave, the device comprising:
   a wave acquiring unit configured to acquire a time waveform of the electromagnetic wave;

a decomposing unit configured to decompose the time waveform of the electromagnetic wave into wavelet expansion coefficients by wavelet transform;

a calculating unit configured to calculate influence levels of the respective wavelet expansion coefficients to a spectrum in a predetermined measurement range;

a weighting unit configured to weight the wavelet expansion coefficients based on at least the influence levels of the respective wavelet expansion coefficients to the spectrum; and a converting unit configured to convert the weighted wavelet expansion coefficients into time waveforms by inverse wavelet transform, wherein the calculating unit
- extracts a single value from the decomposed wavelet expansion coefficients,
- reconstructs the single value into a time waveform by the inverse wavelet transform,
- converts the reconstructed time waveform by Fourier transform,
- calculates a value as one of the influence levels by adding a signal intensity of at least a single frequency; the signal intensity being derived from the Fourier transform, and
- repeats the calculation for the respective wavelet expansion coefficients.

8. An electromagnetic wave measurement method for measuring an electromagnetic wave, the method comprising:

acquiring a time waveform of the electromagnetic wave;

decomposing the time waveform of the electromagnetic wave into wavelet expansion coefficients by wavelet transform;

calculating influence levels of the respective wavelet expansion coefficients to a spectrum in a predetermined measurement range;

weighting the wavelet expansion coefficients, using a processor, based on at least the influence levels of the respective wavelet expansion coefficients to the spectrum; and converting the weighted wavelet expansion coefficients into time waveforms by inverse wavelet transform, wherein the calculation for the influence levels of the respective wavelet expansion coefficients to the spectrum includes:
- extracting a single value of the wavelet expansion coefficients which are decomposed in advance,
- regularizing the value,
- reconstructing the regularized value into a time waveform by the inverse wavelet transform,
- converting the reconstructed time waveform by Fourier transform,
- calculating a value as one of the influence levels by adding a signal intensity of at least a single frequency; the signal intensity being derived from the Fourier transform, and
- repeating the calculation for the respective wavelet expansion coefficients.

9. The electromagnetic wave measurement method according to claim 8, further comprising:

saving as a database the weights of the wavelet expansion coefficients acquired by the weighting on a measurement object basis; and adjusting the weights of the wavelet expansion coefficients depending on the measurement object, wherein, in the conversion, the wavelet expansion coefficients whose weights are adjusted by the adjustment are converted into time waveforms by the inverse wavelet transform.

10. The electromagnetic wave measurement method according to claim 8, wherein, in the weighting, the wavelet expansion coefficients are weighted based on a threshold that is used by the wavelet transform, and the influence levels of the wavelet expansion coefficients to the spectrum.

11. The electromagnetic wave measurement method according to claim 8, wherein the value obtained by adding the signal intensity of the at least single frequency is a value that is obtained by weighting signal intensities of frequencies based on frequencies and adding the signal intensities.

12. The electromagnetic wave measurement method according to claim 8, wherein the electromagnetic wave is a terahertz wave including a frequency component in a range from 30 GHz to 30 THz.

13. A non-transitory storage medium storing a computer-readable program that causes a computer to execute the electromagnetic wave measurement method according to claim 8.

14. An electromagnetic wave measurement device that measures an electromagnetic wave, the device comprising:

a wave acquiring unit configured to acquire a time waveform of the electromagnetic wave;

a decomposing unit configured to decompose the time waveform of the electromagnetic wave into wavelet expansion coefficients by wavelet transform;

a calculating unit configured to calculate influence levels of the respective wavelet expansion coefficients to a spectrum in a predetermined measurement range;

a weighting unit configured to weight the wavelet expansion coefficients based on at least the influence levels of the respective wavelet expansion coefficients to the spectrum; and a converting unit configured to convert the weighted wavelet expansion coefficients into time waveforms by inverse wavelet transform, wherein the calculating unit
- extracts a single value of the wavelet expansion coefficients which are decomposed in advance,
- regularizes the value,
- reconstructs the regularized value into a time waveform by the inverse wavelet transform,
- converts the reconstructed time waveform by Fourier transform,
- calculates a value as one of the influence levels by adding a signal intensity of at least a single frequency; the signal intensity being derived from the Fourier transform, and
- repeats the calculation for the respective wavelet expansion coefficients.

* * * * *